(12) United States Patent
Yin et al.

(10) Patent No.: US 7,128,876 B2
(45) Date of Patent: Oct. 31, 2006

(54) MICRODEVICE AND METHOD FOR COMPONENT SEPARATION IN A FLUID

(75) Inventors: Hongfeng Yin, San Jose, CA (US); Kevin Killeen, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 399 days.

(21) Appl. No.: 09/908,231

(22) Filed: Jul. 17, 2001

(65) Prior Publication Data
US 2003/0017609 A1 Jan. 23, 2003

(51) Int. Cl.
B01L 3/02 (2006.01)
B01L 11/00 (2006.01)
G01N 21/00 (2006.01)
G01N 30/02 (2006.01)
B01D 15/08 (2006.01)

(52) U.S. Cl. ............... 422/100; 422/101; 422/59; 422/60; 422/70; 436/180; 436/177; 210/198.2; 137/625.46

(58) Field of Classification Search .......... 422/99–101, 422/58–60, 70; 210/198.2; 436/180
See application file for complete search history.

(56) References Cited

U.S. PATENT DOCUMENTS

| | | | | |
|---|---|---|---|---|
| 5,154,888 A | * | 10/1992 | Zander et al. | 422/58 |
| 5,291,226 A | | 3/1994 | Schantz et al. | |
| 5,305,015 A | | 4/1994 | Schantz et al. | |
| 5,486,335 A | * | 1/1996 | Wilding et al. | 422/55 |
| 5,565,171 A | * | 10/1996 | Dovichi et al. | 422/68.1 |
| 5,837,546 A | * | 11/1998 | Allen et al. | 436/169 |
| 5,872,010 A | * | 2/1999 | Karger et al. | 436/173 |
| 5,928,880 A | * | 7/1999 | Wilding et al. | 435/7.21 |
| RE36,350 E | * | 10/1999 | Swedberg et al. | 210/198.2 |
| 5,997,708 A | * | 12/1999 | Craig | 204/601 |
| 6,033,628 A | * | 3/2000 | Kaltenbach et al. | 422/68.1 |
| 6,264,892 B1 | * | 7/2001 | Kaltenbach et al. | 422/68.1 |
| 6,375,871 B1 | * | 4/2002 | Bentsen et al. | 264/1.6 |
| 6,454,924 B1 | * | 9/2002 | Jedrzejewski et al. | 204/601 |
| 6,481,453 B1 | * | 11/2002 | O'Conner et al. | 137/15.04 |
| 6,536,477 B1 | * | 3/2003 | O'Connor et al. | 137/833 |
| 6,582,969 B1 | * | 6/2003 | Wagner et al. | 436/518 |
| 6,585,939 B1 | * | 7/2003 | Dapprich | 422/99 |
| 6,627,159 B1 | * | 9/2003 | Bedingham et al. | 422/100 |
| 6,627,406 B1 | * | 9/2003 | Singh et al. | 435/7.1 |

(Continued)

OTHER PUBLICATIONS

U.S. Appl. No. 09/233,694, filed Jan. 19, 1999, Brennen et al.

Primary Examiner—Jill Warden
Assistant Examiner—Brian R. Gordon

(57) ABSTRACT

The present invention relates to a microdevice for separating the components of a fluid sample. A cover plate is arranged over the first surface of a substrate, and, in combination with a microchannel formed in the first surface, defines a separation conduit for separating the components of the fluid sample. A sample inlet port in fluid communication with the conduit allows a fluid sample introduced from a sample source to be conveyed in a defined sample flow path such that the sample fluid travels, in order, through the sample inlet port, the separation conduit and a sample outlet port. The microdevice also includes an integrated introducing means for controllably introducing a volume of the fluid sample from a sample source into the sample inlet port and through the separation conduit. A method for separating the components of a fluid sample using the microdevice is also provided.

19 Claims, 4 Drawing Sheets

U.S. PATENT DOCUMENTS

| | | | |
|---|---|---|---|
| 6,632,619 B1* | 10/2003 | Harrison et al. | 435/7.2 |
| 6,653,625 B1* | 11/2003 | Andersson et al. | 250/288 |
| 6,664,104 B1* | 12/2003 | Pourahmadi et al. | 435/288.6 |
| 6,676,835 B1* | 1/2004 | O'Connor et al. | 210/542 |
| 6,878,271 B1* | 4/2005 | Gilbert et al. | 210/321.61 |
| 6,919,046 B1* | 7/2005 | O'Connor et al. | 422/100 |
| 2001/0036669 A1* | 11/2001 | Jedrzejewski et al. | 436/94 |
| 2002/0037499 A1* | 3/2002 | Quake et al. | 435/5 |
| 2002/0098124 A1* | 7/2002 | Bentsen et al. | 422/100 |
| 2002/0100714 A1* | 8/2002 | Staats | 210/85 |
| 2002/0187557 A1* | 12/2002 | Hobbs et al. | 436/161 |
| 2003/0027352 A1* | 2/2003 | Hooper et al. | 436/169 |
| 2003/0072681 A1* | 4/2003 | Freudenthal et al. | 422/100 |
| 2003/0138359 A1* | 7/2003 | Chow et al. | 422/101 |
| 2003/0150806 A1* | 8/2003 | Hobbs et al. | 210/635 |
| 2003/0223913 A1* | 12/2003 | Karp et al. | 422/101 |
| 2004/0156753 A1* | 8/2004 | Roitman et al. | 422/100 |

* cited by examiner

MICRODEVICE AND METHOD FOR COMPONENT SEPARATION IN A FLUID

TECHNICAL FIELD

The present invention relates to microdevices for component separation in a fluid. More specifically, the invention relates to microdevices that employ an integrated introducing means for controllably introducing a volume of a fluid sample from a sample source into a separation conduit for separating the components of the fluid sample according to a component property.

BACKGROUND

In recent years, microdevice technologies, also referred to as microfluidics and Lab-on-a-Chip technologies, have been proposed for a number of applications in the field of bioanalytical chemistry. Microdevices hold great promise for many applications, particularly in applications that employ rare or expensive fluids, such as proteomics and genomics. The small size of the microdevices allows for the analysis of minute quantities of sample. Having the potential to integrate functions such as sample collection, sample preparation, sample introduction, separation, detection, and compound identification in one device, microdevices such as µ-total analysis systems (µ-TAS) have come to represent the main focus of academic and industrial laboratories research relating to chemical analysis tools or clinical diagnostic tools.

Microdevices having integrated components, e.g., for sample preparation, separation and detection compartments have been proposed in a number of patents. See, e.g., U.S. Pat. No. 5,500,071 to Kaltenbach et al., U.S. Pat. No. 5,571,410 to Swedberg et al., and U.S. Pat. No. 5,645,702 to Witt et al. Because such microdevices have a relatively simple construction, they are in theory inexpensive to manufacture.

Microdevices may be adapted to employ or carry out a number of different separation techniques. Capillary electrophoresis (CE), for example, separates molecules based on differences in the electrophoretic mobility of the molecules. Typically, microdevices employ a controlled application of an electric field to induce fluid flow and or to provide flow switching. In order to effect reproducible and/or high-resolution separation, a fluid sample "plug," a predetermined volume of fluid sample, must be controllably injected into a capillary separation column or conduit. For fluid samples containing high molecular weight charged biomolecular analytes such as DNA fragments and proteins, microdevices containing a capillary electrophoresis separation conduit a few centimeters in length may be effectively used in carrying out sample separation of small volumes of fluid sample having a length on the order of micrometers. Once injected, high sensitivity detection such as laser-induced fluorescence (LIF) may be employed to resolve a separated fluorescently labeled sample component.

For samples containing analyte molecules with low electrophoretic differences, such as those containing small drug molecules, the separation technology of choice is often based on chromatography. Chromatographic separation occurs when a mobile phase carries sample molecules through a chromatography bed (stationary phase) where sample molecules interact with the stationary phase surface. The velocity at which a particular sample component travels through a chromatography bed depends on the component's partition between mobile phase and stationary phase.

There are many chromatographic techniques known in the art. For example, in reverse phase liquid chromatography, where the stationary phase offers a hydrophobic surface and the mobile phase is usually a mixture of water and organic solvent, the least hydrophobic component moves through the chromatography bed first, followed by other components, in order of increasing hydrophobicity. In other words, the chromatographic separation of sample components may be based on hydrophobicity. In isocratic liquid chromatography, the content of the mobile phase is constant throughout the separation. Gradient liquid chromatography, on the other hand, requires the content of the mobile phase to change during separation. Gradient liquid chromatography not only offers high resolution and high-speed separation of wide ranges of compounds, it also allows injection of large sample volumes without compromising separation efficiency. During the initial period when the sample is introduced, the mobile phase strength is often kept low, and the sample is trapped at the head of the liquid chromatography column bed. As a result, interfering moieties such as salts are washed away. In this regard, gradient liquid chromatography is suited to analyze fluid samples containing a low concentration of analyte moieties.

Ordinarily, capillary electrophoresis is not compatible with chromatographic techniques. However, capillary electrochromatography, a fusion of liquid chromatography and capillary electrophoresis involving the application of an electric field in order to generate electroosmotic flow, has been proposed. For example, U.S. Pat. Nos. 5,770,029 and 6,007,690 each to Nelson et al. each describes microdevices employing electroosmotic flow to drive a mobile phase through a high surface area column to achieve sample enrichment. When an electric field is applied, the electroosmotic flow moves the mobile phase through the packed column. However, the charged stationary phase surfaces, e.g., chromatographic bead surfaces, are responsible for generating electrokinetic flow and/or switching as well as separation. Accordingly, capillary electrochromatography suffers from a number of drawbacks. For example, individual control over flow switching and separation is difficult to achieve in capillary electrochromatography. In addition, it is difficult to produce appropriate surfaces for both flow switching and separation for any particular sample. Furthermore, capillary electrochromatography cannot carry out gradient chromatography with reliability, since, as the content of the mobile phase changes during separation, surface charge on the stationary phase associated with electroosmotic flow also change.

Pressure-driven flow associated with conventional liquid chromatography is useful in providing flow through packed columns. A mechanical or other type of pump is typically employed to generate pressure to drive a sample through the column. For example, when particles of 3 to 5 µm diameter are packed, a pressure drop of typically 10–30 bar/cm is used in order to maintain proper fluid flow. However, such pressure-driven flow has not been successfully employed in microdevices for separation.

Since the speed and quality of separation throughput of a microdevice is determined by the precision and accuracy of fluid flow control, there is a need for an improved microdevice that employs a introducing means to controllably introduce a predetermined volume of a fluid sample into a separation column or conduit independent from the microdevice's ability to separate the components of a fluid sample according to a component property. Sample introduction may be performed without need for an electric field. Optionally, such introduction may supplement electrokinetically driven separation. In addition, there is a need for such a microdevice wherein the introducing means represents an integrated portion of the microdevice.

SUMMARY OF THE INVENTION

Accordingly, it is a primary object of the present invention to overcome the above-mentioned disadvantages of the prior art by providing a microdevice that allows for the controllable introduction of a volume of a fluid sample for separation according to a fluid sample component property without need for application of an electric field.

Additional objects, advantages and novel features of the invention will be set forth in part in the description that follows, and in part will become apparent to those skilled in the art upon examination of the following, or may be learned through routine experimentation upon practice of the invention.

In one embodiment, the invention relates to a microdevice for separating the components of a fluid sample. The microdevice comprises a substrate having first and second opposing surfaces, wherein the substrate has a microchannel formed in the first surface. A cover plate is arranged over the first surface and, in combination with the microchannel, defines a separation conduit for separating and/or analyzing the components of the fluid sample according to a component property such as molecular weight, polarity, hydrophobicity or charge. A sample inlet port is provided in fluid communication with the separation conduit to allow a fluid sample introduced from a sample source to be conveyed in a defined sample flow path such that the fluid sample travels, in order, through the sample inlet port, the separation conduit and a sample outlet port. An integrated introducing means is also provided, for controllably introducing a volume, preferably predetermined, of the fluid sample from a sample source into the sample inlet port and through the separation conduit without need for an electric field. The integrated introducing means preferably controls fluid introduction mechanically.

A detector may be interfaced with the microdevice to detect the fluid sample in the flow path or at the sample inlet and outlet ports. The interface of the microdevice may allow a energy source to ionize sample therein. For example, the interface may comprise an electrospray nozzle to deliver sample into an ionization chamber such as those used in mass spectrometers. As another example, the interface may be compatible with laser desorption and ionization technologies. In the alternative or in addition, the interface may be suitable for interfacing with an optical detector, for transmission of electromagnetic radiation of a predetermined wavelength such as ultraviolet, visible or infrared radiation. In one embodiment, the interface is in fluid communication with a collector for collecting the fluid sample downstream from the sample outlet port.

The microdevice may be employed to carry out chromatography. In such a case, a mobile phase source may be provided in fluid communication with the integrated introducing means. In addition, the microdevice may further comprise separation media within separation conduit or a polymeric material formed in situ within the separation conduit. Alternatively, the separation conduit may exhibit a high surface area-to-volume ratio.

The integrated introducing means may comprise a loading chamber sized to hold the predetermined volume of fluid sample, the loading chamber constructed for allowing switchable fluid communication with either the sample source or the mobile phase source. Switchable fluid communication may be achieved through a sliding and preferably rotational motion, though linear sliding motion may be employed in the alternative. The integrated introducing means may provide fluid communication with the mobile phase source through a bypass with the separation conduit when the loading chamber is in fluid communication with the sample source. In addition, the microdevice may further comprise a flow rate regulator such as a flow splitter for regulating fluid flow rate between the mobile phase source and the integrated introducing means. The mobile phase source may include a mixer for mixing solvents and/or a flow sensor for determining and optionally controlling the rate of flow into the sample inlet source.

In another embodiment, the substrate of the microdevice has a first and a second microchannel formed in the first surface. When a cover plate is arranged over the first surface, the cover plate in combination with the first and second microchannels defines a first and a second conduit, respectively. At least one of the conduits is constructed for separating the components of the fluid sample according to a component property. A sample inlet port is provided in fluid communication with a valve, wherein the valve is constructed for providing selective fluid communication from the inlet port to either one of the conduits to allow a fluid sample introduced from a sample source to be conveyed in a defined sample flow path such that the sample travels, in order, through the sample inlet port, the selected conduit and a sample outlet port associated with the conduit. Also provided is an integrated introducing means for controllably introducing a predetermined volume of the fluid sample from a sample source into the sample inlet port. Optionally, each of the conduits is constructed for separating the components of the fluid sample according to a different component property.

In a further embodiment, two introducing means are provided—a first integrated introducing means for controllably introducing the fluid sample from a sample source through a sample inlet port in fluid communication with the first conduit and a second integrated introducing means for controllably introducing fluid sample from the first conduit through the second conduit and an outlet port.

In still another embodiment, the invention relates to a method for separating the components of a fluid sample. The method involves providing a microdevice comprising: a substrate having first and second opposing surfaces, with a microchannel formed in the first surface; a cover plate arranged over the first surface which in combination with the microchannel defines a conduit for separating the components of the fluid sample according to a component property; and a sample inlet port in fluid communication with the conduit, wherein the sample inlet port allows a fluid sample introduced from a sample source to be conveyed in a defined sample flow path such that the sample travels, in order, through the sample inlet port, the conduit and a sample outlet port. A predetermined volume of the fluid sample is controllably introduced from the sample source into the sample inlet port and conveyed through the conduit, thereby separating the components of the fluid sample. The fluid sample flowing in the flow path or from the sample outlet port is analyzed after optional collection downstream from the sample outlet port.

BRIEF DESCRIPTION OF THE DRAWINGS

FIG. 1A illustrates the device in exploded view. FIGS. 1B and 1C schematically illustrate the microdevice in first and second flow path configurations, respectively.

FIG. 2A schematically illustrate the microdevice. FIG. 2B illustrate an example of the valve plate that may be employed to effect flow switching between the parallel conduits.

DETAILED DESCRIPTION OF THE INVENTION

Figure 1A:
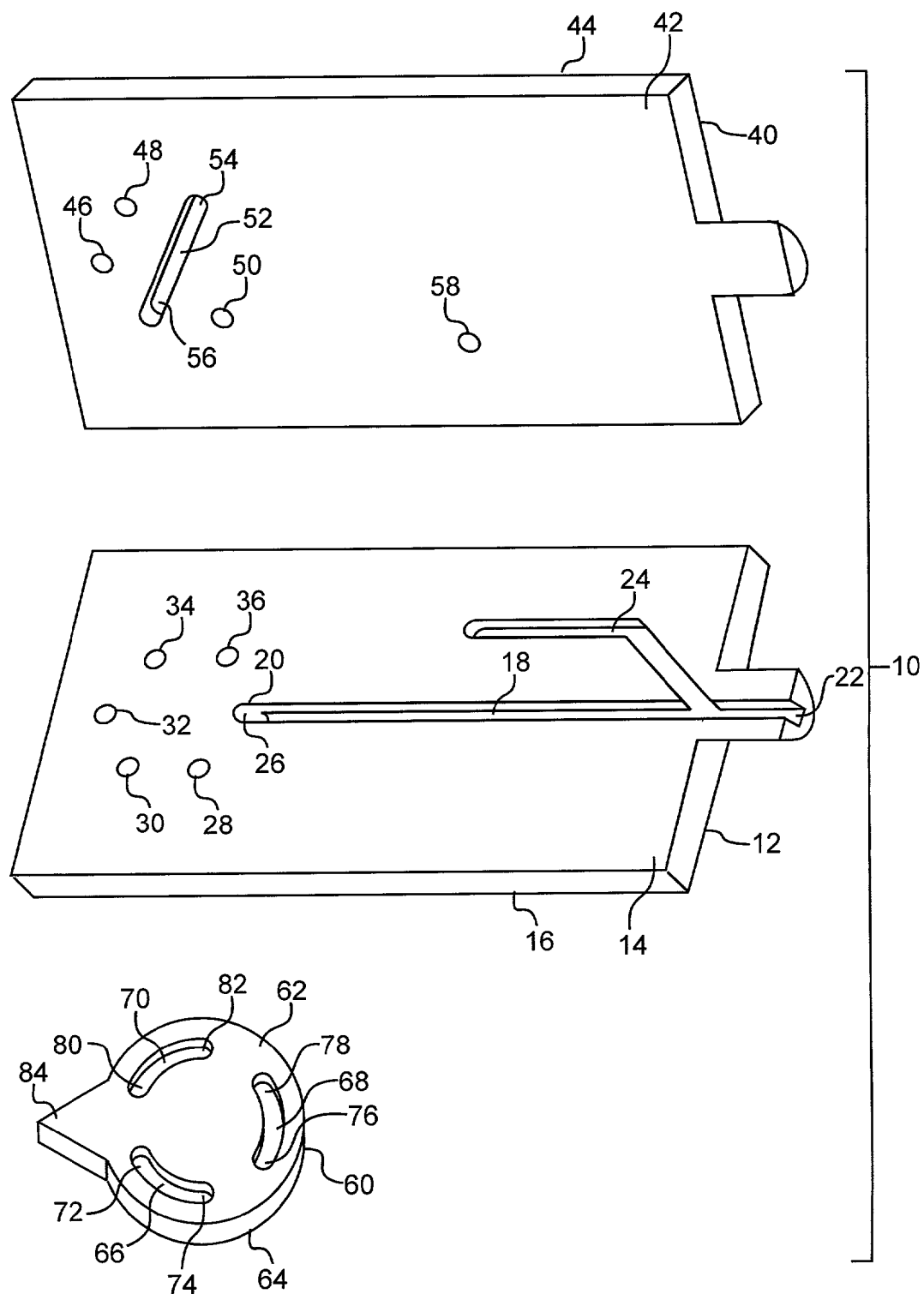
FIGS. 1A–1C, collectively referred to as FIG. 1, illustrate a microdevice having an integrated introducing means that employs the rotational sliding motion of a switching plate in order to effect fluid communication between fluid-transporting features.

Before the invention is described in detail, it is to be understood that unless otherwise indicated this invention is not limited to particular materials, components or manufacturing processes, as such may vary. It is also to be understood that the terminology used herein is for purposes of describing particular embodiments only, and is not intended to be limiting.

It must be noted that, as used in the specification and the appended claims, the singular forms "a," "an" and "the" include plural referents unless the context clearly dictates otherwise. Thus, for example, reference to "a microchannel" includes a plurality of microchannels, reference to "a fluid" includes a mixture of fluids, reference to "a component property" includes a plurality of component properties and the like.

In this specification and in the claims that follow, reference will be made to a number of terms that shall be defined to have the following meanings:

The term "constructed" as used herein refers to forming, assembling, modifying or combining components in order to build at least a portion of the inventive microdevice. Thus, "a conduit constructed for separating" as used herein refers to assembling or combining parts to form a conduit or modifying a surface of a conduit, wherein the conduit serves to differentiate or discriminate sample fluid components. For example, a conduit constructed for separating the components of a fluid sample may have a chemically, mechanically or energetically modified interior surface that interacts with different components differently, or may contain separating media such as chromatographic packing material.

The term "controllably introduce" as used herein refers to the delivery of a predetermined volume of a fluid sample in a precise and accurate manner. A fluid sample may be "controllably introduced" through controllable alignment of two components of a microdevice, i.e., fluid-transporting features.

The term "flow path" as used herein refers to the route or course along which a fluid travels or moves. Flow paths are formed from one or more fluid-transporting features of a microdevice.

The term "fluid-transporting feature" as used herein refers to an arrangement of solid bodies or portions thereof that direct fluid flow. Fluid-transporting features include, but are not limited to, chambers, reservoirs, conduits and channels. The term "conduit" as used herein refers to a three-dimensional enclosure formed by one or more walls and having an inlet opening and an outlet opening through which fluid may be transported. The term "channel" is used herein to refer to an open groove or a trench in a surface. A channel in combination with a solid piece over the channel forms a conduit.

The term "fluid-tight" is used herein to describe the spatial relationship between two solid surfaces in physical contact such that fluid is prevented from flowing into the interface between the surfaces.

The term "in order" is used herein to refer to a sequence of events. When a fluid travels "in order" through an inlet port and a conduit, the fluid travels through the inlet port before traveling through the conduit. "In order" does not necessarily mean consecutively. For example, a fluid traveling in order through an inlet port and outlet port does not preclude the fluid from traveling through a conduit after traveling through the inlet port and before traveling through the outlet port.

The term "microalignment means" is defined herein to refer to any means for ensuring the precise microalignment of microfabricated features in a microdevice. Microalignment means can be formed either by laser ablation or by other methods of fabricating shaped pieces well known in the art. Representative microalignment means that can be employed herein include a plurality of appropriately arranged protrusions in component parts, e.g., projections, depressions, grooves, ridges, guides, or the like.

The term "microdevice" refers to a device having features of micron or submicron dimensions, and which can be used in any number of chemical processes involving very small amounts of fluid. Such processes include, but are not limited to, electrophoresis (e.g., capillary electrophoresis or CE), chromatography (e.g., μLC), screening and diagnostics (using, e.g., hybridization or other binding means), and chemical and biochemical synthesis (e.g., DNA amplification as may be conducted using the polymerase chain reaction, or "PCR") and analysis (e.g., through enzymatic digestion). The features of the microdevices are adapted to the particular use. For example, microdevices that are used in separation processes, e.g., CE, contain microchannels (termed "microconduits" herein when enclosed, i.e., when the cover plate is in place on the microchannel-containing substrate surface) on the order of 1 μm to 200 μm in diameter, typically 10 μm to 75 μm in diameter, and approximately 0.1 to 50 cm in length. Microdevices that are used in chemical and biochemical synthesis, e.g., DNA amplification, will generally contain reaction zones (termed "reaction chambers" herein when enclosed, i.e., again, when the cover plate is in place on the microchannel-containing substrate surface) having a volume of about 1 nl to about 100 μl, typically about 10 nl to 20 μl.

"Optional" or "optionally" as used herein means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Thus, the invention generally relates to a microdevice for separating the components of a fluid sample. The microdevice is constructed from a substrate having first and second opposing surfaces, wherein the substrate has a microchannel formed in the first surface. A cover plate is arranged over the first surface and, in combination with the microchannel, defines a separation conduit for separating the components of the fluid sample according to a component property. A sample inlet port is provided in fluid communication with the conduit to allow a fluid sample introduced from a sample source to be conveyed in a defined sample flow path such that the sample travels, in order, through the sample inlet port, the separation conduit and a sample outlet port. An integrated introducing means is provided for controllably introducing a volume of the fluid sample from a sample source into the sample inlet port. In contrast to previously proposed microseparation devices, which have a motive force means that may fail to provide for adequate control over fluid sample introduction, the integrated introducing means herein provides for improved separation performance in terms of throughput and resolution.

FIG. 1 illustrates an embodiment of the inventive microdevice having an integrated introducing means in combination with an integrated separation column for liquid chromatography. As with all figures referenced herein, in which like parts are referenced by like numerals, FIG. 1 is not necessarily to scale, and certain dimensions may be exaggerated for clarity of presentation. The microdevice 10 employs a switching structure that employs rotational motion to controllably introduce a predetermined volume of fluid sample. As illustrated in FIG. 1A, the microdevice 10 includes a substrate 12 comprising first and second substantially planar opposing surfaces indicated at 14 and 16, respectively, and is comprised of a material that is substantially inert with respect to fluids that will be transported through the microdevice. The substrate 12 has a fluid-transporting feature in the form of a sample microchannel 18 in the first planar surface 14. The sample microchannel 18 represents a portion of a separation conduit 25 as discussed below. The fluid-transporting feature may be formed through laser ablation or other techniques discussed below or known in the art. It will be readily appreciated that although the sample microchannel 18 has been represented in a generally extended form, sample microchannels for this and other embodiments can have a variety of configurations, such as a straight, serpentine, spiral, or any tortuous path. Further, as described above, the sample microchannel 18 can be formed in a wide variety of channel geometries, including semi-circular, rectangular, rhomboid, and the like, and the channels can be formed in a wide range of aspect ratios. A device may also have a plurality of sample microchannels. The sample microchannel 18 has a sample inlet terminus 20 at a first end and a sample outlet terminus 22 at the opposing end. As shown in FIG. 1, the sample outlet terminus is located at a protrusion of the otherwise rectangular substrate 12. In addition, an optional make-up fluid microchannel 24 is also formed in the first planar surface 14 in fluid communication with the sample microchannel 18, downstream from the sample inlet terminus 20 and upstream from the sample outlet terminus 22. Located at the sample inlet terminus 20 is a cylindrical conduit 26 that extends through surface 16. Five additional cylindrical conduits, 28, 30, 32, 34, 36 also extend through substrate 12 and, in combination with conduit 26, represent the vertices of an equilateral hexagon.

The microdevice 10 also includes a cover plate 40 that is complementarily shaped with respect to the substrate 12 and has first and second substantially planar opposing surfaces indicated at 42 and 44, respectively. The contact surface 42 of the cover plate 40 is capable of interfacing closely with the contact surface 14 of the substrate 12 to achieve fluid-tight contact between the surfaces. The cover plate 40 is substantially immobilized over the substrate contact surface 14, and the cover plate contact surface 42 in combination with the sample microchannel 18 defines a sample conduit 25 for conveying the sample. Similarly, the cover plate 40, and in combination with the make-up fluid channel 24, defines a make-up fluid conduit 27 for conveying make-up fluid from a make-up fluid source (not shown) to the fluid sample conduit. Because the contact surfaces of the cover plate and the substrate are in fluid-tight contact, the sample conduit and the make-up fluid conduit are fluid tight as well. The cover plate 40 can be formed from any suitable material for forming the substrate 12 as described below. Further, the cover plate 40 can be aligned over the substrate contact surface 14 by any of a number of microalignment means. To ensure that the sample conduit is fluid-tight, pressure-sealing techniques may be employed, e.g., by using external means (such as clips, tension springs or an associated clamp), by using internal means (such as male and female couplings) or by using of chemical means (e.g., adhesive or welding) to urge the pieces together However, as with all embodiments described herein the pressure sealing techniques may allow the contacts surfaces to remain in fluid-tight contact under an internal microdevice fluid pressure of up to about 100 megapascals, typically about 0.5 to about 40 megapascals.

As shown in FIG. 1A, the cover plate 40 and the substrate 12 may be discrete components. In such a case, microalignment means described herein or known to one of ordinary skill in the art may be employed to align the cover plate with the substrate. In some instances, however, the substrate and the cover plate may be formed in a single, solid flexible piece. Microdevices having a single-piece substrate and cover plate configuration have been described, e.g., in U.S. Pat. Nos. 5,658,413 and 5,882,571, each to Kaltenbach et al.

The cover plate 40 may include a variety of features. As shown, a sample inlet port 46 is provided as a cylindrical conduit extending through the cover plate in a direction orthogonal to the cover plate contact surface 42 to provide communication between surfaces 42 and 44. Although axial symmetry and orthogonality are preferred, the sample inlet port 46 does not have to be axially symmetrical or extend in an orthogonal direction with respect to the cover plate contact surface. The inlet port 46 can be arranged to communicate with the conduit 32 of the substrate 12. As shown, the inlet port 46 has a substantially constant cross-sectional area along its length. The sample inlet port 46 enables passage of fluid from an external source (not shown) through conduit 32 to communicate with switching plate 60 as discussed below. The cross-sectional area of the inlet port should correspond to the cross-sectional area and shape of conduit 32. Similarly, two additional cylindrical conduits, i.e., waste port 48 and mobile phase inlet port 50 are provided fluid communication with conduit 30 and 36, respectively. Further, make-up fluid port 40 is also provided to allow make-up fluid from a make-up fluid source to be introduced into make-up fluid conduit 28.

A linear channel 52 having two termini, indicated at 54 and 56, is located in contact surface 42. The termini 54, 56 fluidly communicate with conduits 34, 28, respectively. The termini 54 and 56 in combination with conduits 46, 48 and 50 represent five of six vertices of an equilateral hexagon. Accordingly, each of the conduits is located the same distance from the center point of the channel 52. As discussed above, the cover plate 40 is substantially immobilized over the substrate contact surface 14. As a result, substrate surface 14 in combination with channel 52 forms a conduit 53, which serves as a sample-loading chamber, discussed below. Alternatively, the linear channel 52 may be provided on substrate surface 14. In such a case, termini 54 and 56 would coincide in location with conduits 34 and 28 respectively.

The sample conduit 25 is constructed for separation, and the device may therefore exhibit any micromachined structure appropriate for liquid chromatography. For example, U.S. Pat. No. 6,156,273 describes a micromachined liquid chromatography structure with a mass spectrometer interface. In addition, the conduit may contain any of a number of known liquid chromatographic packing materials may be included in the sample conduit. Such packing materials typically exhibit a surface area of about 100 to about 500 $m^2/g$. The conduit 25, for example, may be adapted to separate fluid sample components according to molecular weight, polarity, hydrophobicity or other properties through techniques known to one of ordinary skill in the art, e.g., through proper selection of packing materials. In addition or in the alternative, the interior surface of the conduit may be chemically, mechanically or otherwise modified using techniques known in the art to carry out separation of the components of a fluid sample according to a selected property. For example, U.S. Ser. No. 09/233,694 ("A Method for Producing High-Surface Area Texturing of a Substrate, Substrates Prepared Thereby and Masks for Use Therein"), inventors Brennen and Swedberg, filed on Jan. 19, 1999, describes a laser ablated high surface area microchannel; U.S. Pat. No. 5,770,029 describes a electrophoretic microdevice that allows for integrated sample enrichment means using a high surface area structure; U.S. Pat. No. 5,334,310 describes an microchannel having in-situ generated polymer therein. Thus, the interior surface of the conduit may exhibit surface characteristics such adsorption properties and surface area similar to that associated with packing materials. In any case, typical samples may contain biomolecules such as nucleotidic and/or peptidic moieties.

A switching plate 60 is provided as a means for delivering a predetermined volume of fluid sample. This switching plate 60 is similar to that described in U.S. Ser. No. 09/908,292, now issued as U.S. Pat. No. 6,702,256 ("Flow-Switching Microdevice") inventors Killeen and Yin, filed on even date herewith.

As shown in FIG. 1A, the switching plate 60 has a substantially planar and circular contact surface 62 and an opposing contact surface 64. As shown, the surfaces 62 and 64 are generally congruent. Three curved fluid-transporting channels, indicated at 66, 68 and 70, are each located on contact surface 62. The fluid-transporting features lie along a circle having a diameter equal to the length of channel 52. Each fluid-transporting channel has two termini: termini 72 and 74 are associated with feature 66, termini 76 and 78 are associated with feature 68, and termini 80 and 82 are associated with feature 70. An optional handle 84 that provides for ease in manipulation of the switching plate 60 extends outwardly from the center of the channels.

The switching plate contact surface 62 may be placed in slidable and fluid-tight contact with substrate surface 16. As a result, the fluid-transporting channels, 66, 68 and 70, in combination with substrate surface 16, form three curved conduits, 67, 69, 71, respectively.

Figure 1B:
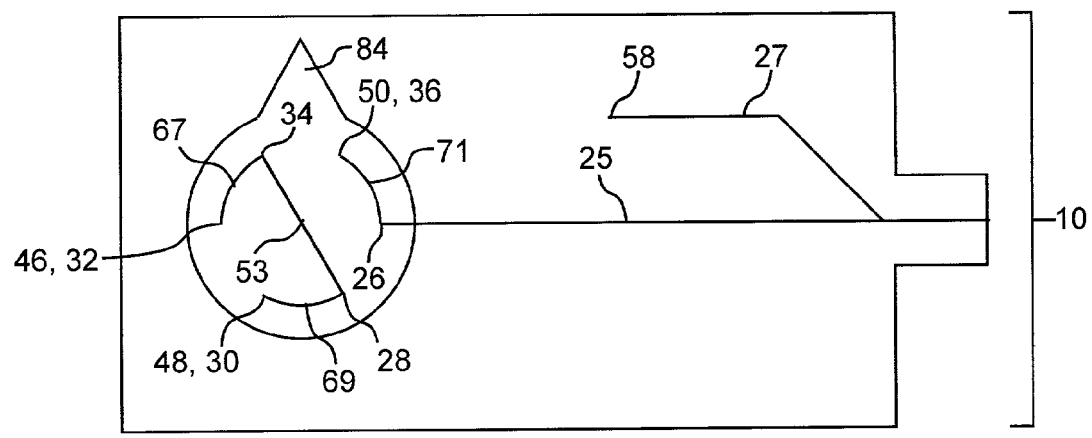
Figure 1C:
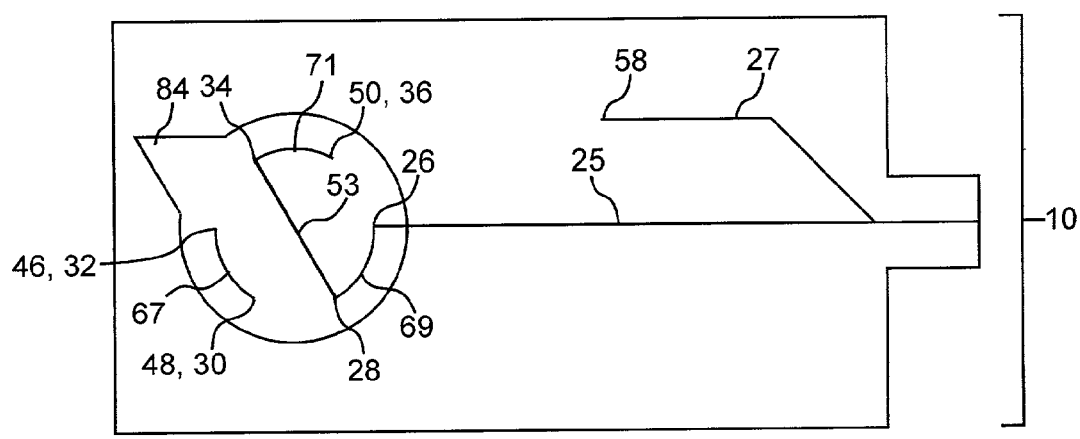

Depending on the relative orientation of the switching plate and the substrate, at least two possible flow paths configurations can be created. As shown in FIG. 1B, the first flow path configuration allows a fluid originating from sample inlet port 46 to travel, in order, through conduit 32, conduit 67, conduit 34, conduit 53, conduit 28, conduit 69, conduit 30 and waste port 48. The first flow path configuration also allows a fluid originating from mobile phase inlet port 50 to travel, in order, through conduit 36, conduit 71, conduit 26 and conduit 25. By rotating the switching plate 60 60° about its center, a second flow path configuration results, as shown in FIG. 1C. The second flow path configuration allows fluid originating from sample inlet port 46 to travel, in order, through conduit 32, conduit 67, conduit 30, and waste port 48. In addition, the second flow path configuration allows fluid originating from conduit 50 to travel, in order, through conduit 36, conduit 70, conduit 34, conduit 53, conduit 28, conduit 69, conduit 26 and sample conduit 25.

In use, the microdevice operates in a manner similar to a simple capillary liquid chromatographic apparatus. The switching plate 60 of the microdevice is arranged to result in a first flow path configuration as discussed above. A pump generates a high-pressure gradient to deliver a mobile phase through mobile phase inlet port 50, conduit 36, conduit 71, conduit 26 and conduit 25. In order to control the internal pressure of the microdevice and the flow rate of the mobile phase, a splitter, integrate or otherwise, may be employed to divert a portion of the mobile phase before entry into the conduit 50. In addition, fluid sample is injected into sample inlet port 46 from a sample source. As a result, the fluid sample forms a contiguous body of fluid that flows, through sample inlet port 46 conduit 32, conduit 67, conduit 34, conduit 53, conduit 28, conduit 69, conduit 30 and waste port 48. The sample emerging from conduit 66 may be collected and recycled.

Figure 2A:
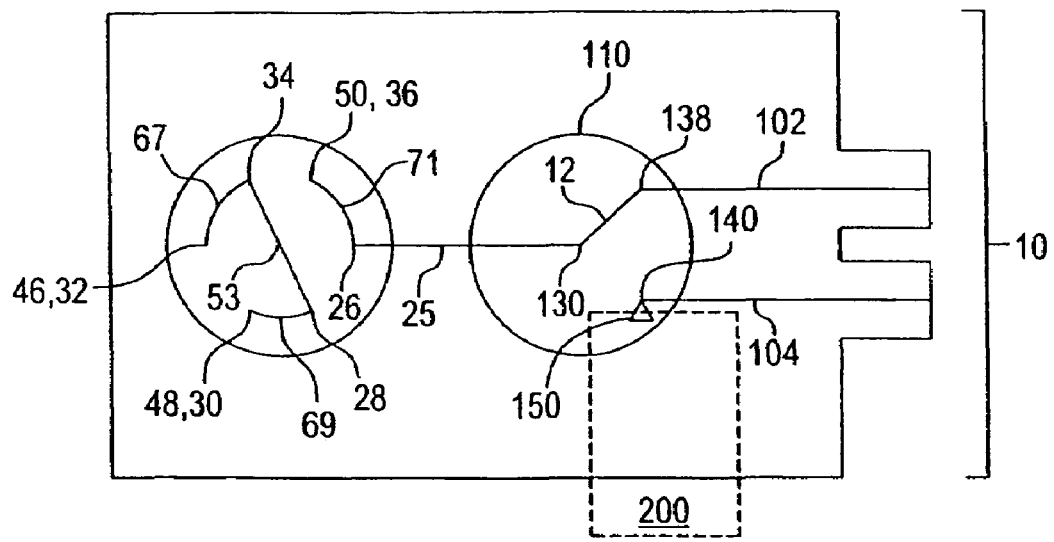
FIGS. 2A and 2B, collectively referred to as FIG. 2, illustrate another embodiment of the inventive microdevice that employs two parallel conduits.

By forming a second flow path configuration as discussed above, the conduit 53 is now positioned in the flow path of the mobile phase entering the microdevice through conduit 50. That is, the mobile phase is now pumped through a flow path that travels, in order, through conduit 50, conduit 36, conduit 70, conduit 34, conduit 53, conduit 28, conduit 69, conduit 26 and sample conduit 25. Thus, fluid sample remaining within conduit 53 is also forced through separation conduit 25. It should be evident, then, that by rotating the substrate of the switching assembly, a predetermined volume of fluid sample defined by conduit 53 is controllably introduced from a sample source into the separation conduit 25 of microdevice 10. The sample plug is then separated into sample components according to a component property and emerges from sample outlet port. The outlet may be interfaced with a collector, such as a sample vial, plate or capillary. The collector may serve as a storage device or represent an intermediary to another device that uses and/or analyzes collected fraction. Alternatively, an analytical device 200 may be directly interfaced with the outlet port 140 for fraction analysis (FIG. 2A).

It should be noted that an analyzer may be interfaced with any portion of the flow path of the inventive microdevice including in the inlet port. The analyzer may be, for example, a mass spectrometer, in which case the outlet port may be located within or adapted to deliver fluid sample to an ionization chamber by, for example, electrospray nozzle 49 (FIG. 1C). See U.S. Ser. No. 09/711,804 ("A Microdevice Having an Integrated Protruding Electrospray Emitter and a Method for Producing the Microdevice"), inventors Brennen, Yin and Killeen, filed on Nov. 13, 2000. In addition, mass spectrometry technologies are well known in the art and may involve, for example, laser desorption and ionization technologies, whose use in conjunction with microdevices are described in U.S. Pat. Nos. 5,705,813 and 5,716,825. In the alternative or in addition, the analyzer may be a source of electromagnetic radiation configured to generate electromagnetic radiation of a predetermined wavelength. Depending on the intrinsic properties of the fluid sample and/or any molecular labels used, the radiation may be ultraviolet, visible or infrared radiation.

It should also be noted that other aspects of known separation technology may be incorporated in the practice of the present invention. For example, when ordinary liquid chromatography packing material is slurry packed within the separation conduit, a frit structure, micromachined or otherwise, may be included near or at the sample outlet port. The frit structure serves to ensure that the packing material is not displaced from within the sample conduit when a fluid sample and/or a mobile phase are conveyed through the conduit. In addition, it is preferred that the cross-sectional area of the separation conduit is reduced downstream from the frit structure, particularly if the sample outlet port 140 is a part of an electrospray tip 150 as described, for example, in U.S. Ser. No. 09/711,804 ("A Microdevice Having an Integrated Protruding Electrospray Emitter and a Method for Producing the Microdevice"), inventors Brennen, Yin and Killeen, filed on Nov. 13, 2000, and as shown for example in FIG. 2A.

In addition, multiple liquid chromatography columns can be included in a single microdevice. Such microdevices may involve parallel sample introduction from one or a plurality of sample sources followed by serial separation or parallel sample separation. Thus, in another embodiment, the invention relates to a microdevice for separating the components of a fluid sample having at least one additional microchannel. In this embodiment, a first and a second microchannel are formed in the first surface and the cover plate in combination with the first and second microchannels defining a first and a second conduit, respectively. The sample inlet port is in fluid communication with a valve and the valve is constructed for providing selective fluid communication between the inlet port and either one of the conduits. As a result, a fluid sample introduced from a sample source can be conveyed in a defined sample flow path that travels, in order, through the sample inlet port, the selected conduit, and a sample outlet port associated with the selected conduit. At least one of the conduits is constructed for separating the components of the fluid sample according to a component property. Preferably, each of the conduits is constructed for separating the components of the fluid sample according to a different component property.

This embodiment is illustrated in FIG. 2. This embodiment is similar to that illustrated in FIG. 1 in that the microdevice 10 employs a switching structure that uses rotational and sliding motion to controllably introduce a predetermined volume of fluid sample to a separation conduit. However, in this embodiment, the microdevice includes additional features as well. As illustrated in FIG. 2, additional conduits indicated at 102 and 104 are provided downstream from conduit 25. A valve 110 is interposed between conduit 25 and additional conduits 102 and 104. The valve 110 is constructed for allowing a fluid sample to flow from conduit 25 to no more than one of conduits 102 and 104 at a time.

Figure 2B:
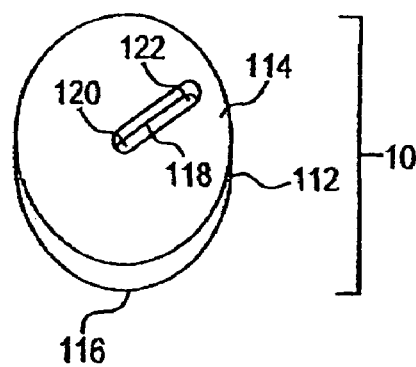

A variety of valve types known in the art can be employed to selectively provide fluid communication between conduit 25 and conduits 102 and 104. Known valve types include, but are not limited to, ball valves, solenoid valves and gate valves. It is preferred that the valve is constructed as an integrated portion of the inventive microdevice. Thus, as illustrated in FIG. 2B, the valve 110 may include a cylindrical valve plate 112 having a contact surface 114 and an exterior surface 116. In such a case, the contact surface 114 and the exterior surface 116 of the valve plate are typically substantially planar opposing. The valve plate 112 has a fluid-transporting feature in the form of a valve microchannel 118 in the first planar surface 114. The valve microchannel 118 has an inlet terminus 120 at one end and an outlet terminus 122 at another end. The inlet terminus 120 is located at the center of the circular substrate surface 114, while the outlet terminus 122 is closer to the edge of the valve plate 112. When the contact surface of the valve plate is placed in fluid-tight contact with an exterior surface of either the substrate 12 of the cover plate 40, the exterior surface in combination with the microchannel forms a fluid-tight valve conduit 119.

In this configuration, either the cover plate or the substrate includes a valve inlet port 130 and valve outlet ports 138 and 140 as cylindrical conduits extending therethrough. The valve inlet port 130 is positioned to allow fluid to flow from the downstream terminus of the conduit 25 and the inlet terminus 120 of the valve microchannel. Although axial symmetry and orthogonality are preferred, the valve inlet port does not have to be axially symmetrical or extend in an orthogonal direction with respect to the substrate contact surface. The inlet port 130 may have a substantially constant cross-sectional area along its length, and the cross-sectional area of the inlet port should correspond to the width of the valve microchannel 118 and to the shape of the microchannel at the inlet terminus 120.

The valve outlet ports are located the same distance from the valve outlet port, the distance being the length of valve microchannel. The valve outlet ports 138 and 140 are positioned to allow fluid to flow to conduits 102 and 104, respectively. By rotating valve plate 112, selective fluid communication can be provided between inlet port 130 and conduits 102 and 104. As discussed above, each conduit may be provided with different packing materials selected according to the fluid sample and the desired separation technique.

Instead of carrying out parallel separation, multiple liquid chromatography columns can be included in a single microdevice to carry out multidimensional separations, i.e., separation in series. Thus, in another embodiment, a microdevice is provided that includes a first integrated introducing means for controllably introducing the fluid sample from a sample source through a sample inlet port in fluid communication with the first conduit, and a second integrated introducing means for controllably introducing fluid sample from the first conduit through the second conduit and an outlet port. At least one of the conduits is constructed for separating the fluid according to a component property. In this embodiment, then, a flow path joins at least one additional conduit in series with a separation conduit and thus provides for multidimensional separation providing that at least one additional conduit is adapted for separation.

Figure 3:
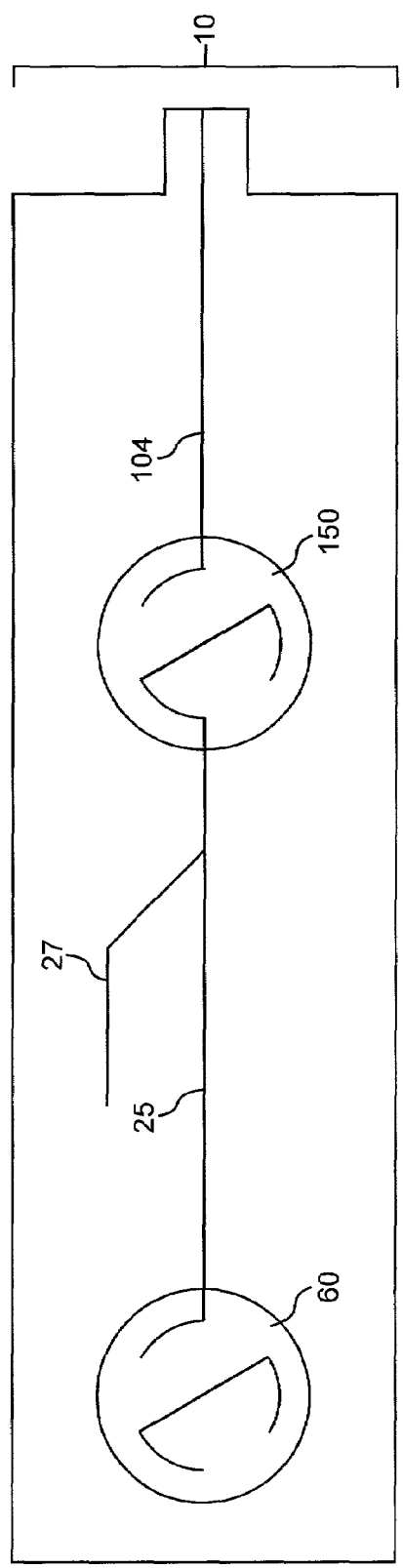
FIG. 3 schematically illustrates a further embodiment of the inventive microdevice that may be used to carry out separation in series.

This embodiment is illustrated in FIG. 3. Microdevice 10 includes a introducing means in the form of a switching plate 60 as illustrated in FIG. 1 that employs rotational motion to controllably introduce a predetermined volume of fluid sample in to a separation conduit. The microdevice includes a second integrated introducing means 150 for controllably introducing fluid sample from the first conduit. The second integrated introducing means 150 may be of the same or different construction as the switching assembly discussed above. In addition, as illustrated in FIG. 3, an additional conduit 104 is provided downstream from the inlet port. This additional conduit may be employed in a second dimensional separation. For example, the first conduit may provide a first dimension of separation for nucleotidic or peptidic moieties through size exclusion chromatography, ion chromatography, capillary electrophoresis, isoelectric focusing, or electrophoretic focusing via field gradient. Then, fractions from the first dimension separation can be directed into an optional reaction chamber within the integrated introducing means filled with a reaction catalyst, e.g., in the form of catalyst-modified beads. In this case, proteins are separated in the first dimension and they are then subjected to digestion in the reaction chamber, followed by second dimension separation in the secondary conduit.

In any of the above embodiments, suitable materials for forming the substrates and cover plates are selected with regard to physical and chemical characteristics that are desirable for proper functioning of the microdevice. In all cases, the substrate must be fabricated from a material that enables formation of high definition (or high "resolution") features, i.e., microchannels, chambers and the like, that are of micron or submicron dimensions. That is, the material must be capable of microfabrication using, e.g., dry etching, wet etching, laser etching, laser ablation, molding, embossing, or the like, so as to have desired miniaturized surface features; preferably, the substrate is capable of being microfabricated in such a manner as to form features in, on and/or through the surface of the substrate. Microstructures can also be formed on the surface of a substrate by adding material thereto, for example, polymer channels can be formed on the surface of a glass substrate using photo-imageable polyimide. Also, all device materials used should be chemically inert and physically stable with respect to any substance with which they come into contact when used to introduce a fluid sample (e.g., with respect to pH, electric fields, etc.). Suitable materials for forming the present devices include, but are not limited to, polymeric materials, ceramics (including aluminum oxide and the like), glass, metals, composites, and laminates thereof.

Polymeric materials are particularly preferred herein, and will typically be organic polymers that are either homopolymers or copolymers, naturally occurring or synthetic, crosslinked or uncrosslinked. Specific polymers of interest include, but are not limited to, polyimides, polycarbonates, polyesters, polyamides, polyethers, polyurethanes, polyfluorocarbons, polystyrenes, poly(acrylonitrile-butadiene-styrene)(ABS), acrylate and acrylic acid polymers such as polymethyl methacrylate, and other substituted and unsubstituted polyolefins, and copolymers thereof. Generally, at least one of the substrate or cover plate comprises a biofouling-resistant polymer when the microdevice is employed to transport biological fluids. Polyimide is of particular interest and has proven to be a highly desirable substrate material in a number of contexts. Polyimides are commercially available, e.g., under the tradename Kapton®, (DuPont, Wilmington, Del.) and Upilex® (Ube Industries, Ltd., Japan). Polyetheretherketones (PEEK) also exhibit desirable biofouling resistant properties.

The devices of the invention may also be fabricated from a "composite," i.e., a composition comprised of unlike materials. The composite may be a block composite, e.g., an A-B-A block composite, an A-B-C block composite, or the like. Alternatively, the composite may be a heterogeneous combination of materials, i.e., in which the materials are distinct from separate phases, or a homogeneous combination of unlike materials. As used herein, the term "composite" is used to include a "laminate" composite. A "laminate" refers to a composite material formed from several different bonded layers of identical or different materials. Other preferred composite substrates include polymer laminates, polymer-metal laminates, e.g., polymer coated with copper, a ceramic-in-metal or a polymer-in-metal composite. One preferred composite material is a polyimide laminate formed from a first layer of polyimide such as Kapton®, that has been co-extruded with a second, thin layer of a thermal adhesive form of polyimide known as KJ®, also available from DuPont (Wilmington, Del.).

The present microdevices can be fabricated using any convenient method, including, but not limited to, micromolding and casting techniques, embossing methods, surface micro-machining and bulk-micromachining. The latter technique involves formation of microstructures by etching directly into a bulk material, typically using wet chemical etching or reactive ion etching ("RIE"). Surface micromachining involves fabrication from films deposited on the surface of a substrate. An exemplary surface micro-machining process is known as "LIGA." See, for example, Becker et al. (1986), "Fabrication of Microstructures with High Aspect Ratios and Great Structural Heights by Synchrotron Radiation Lithography Galvanoforming, and Plastic Moulding (LIGA Process)," *Microelectronic Engineering* 4(1): 35–36; Ehrfeld et al. (1988), "1988 LIGA Process: Sensor Construction Techniques via X-Ray Lithography," *Tech. Digest from IEEE Solid-State Sensor and Actuator Workshop,* Hilton Head, S. C.; Guckel et al. (1991) *J. Micromech. Microeng.* 1: 135–138. LIGA involves deposition of a relatively thick layer of an X-ray resist on a substrate followed by exposure to high-energy X-ray radiation through an X-ray mask, and removal of the irradiated resist portions using a chemical developer. The LIGA mold so provided can be used to prepare structures having horizontal dimensions—i.e., diameters—on the order of microns.

Another technique for preparing the present microdevices is laser ablation. In laser ablation, short pulses of intense ultraviolet light are absorbed in a thin surface layer of material. Preferred pulse energies are greater than about 100 millijoules per square centimeter and pulse durations are shorter than about 1 microsecond. Under these conditions, the intense ultraviolet light photo-dissociates the chemical bonds in the substrate surface. The absorbed ultraviolet energy is concentrated in such a small volume of material that it rapidly heats the dissociated fragments and ejects them away from the substrate surface. Because these processes occur so quickly, there is no time for heat to propagate to the surrounding material. As a result, the surrounding region is not melted or otherwise damaged, and the perimeter of ablated features can replicate the shape of the incident optical beam with precision on the scale of about one micron or less. Laser ablation will typically involve use of a high-energy photon laser such as an excimer laser of the $F_2$, ArF, KrCl, KrF, or XeCl type. However, other ultraviolet light sources with substantially the same optical wavelengths and energy densities may be used as well. Laser ablation techniques are described, for example, by Znotins et al. (1987) *Laser Focus Electro Optics,* at pp. 54–70, and in U.S. Pat. Nos. 5,291,226 and 5,305,015 to Schantz et al.

The fabrication technique that is used must provide for features of sufficiently high definition, i.e., microscale components, channels, chambers, etc., such that precise "microalignment" of these features is possible, i.e., the features must be capable of precise and accurate alignment, including, for example, the alignment of complementary microchannels with each other, the alignment of projections and mating depressions, the alignment of grooves and mating ridges, and the like.

In addition to the switching assembly, other integrated introducing means may also be employed. Typically, an integrated introducing means comprises a loading chamber sized to hold a predetermined volume of fluid sample. By constructing the loading chamber to allow for switchable fluid communication with either the sample source or the mobile phase source, a predetermined volume of fluid sample may be loaded into the chamber or removed therefrom. That is, the loading chamber assists in the accurate and precise handing of a predetermined volume of fluid sample. In addition, the loading chamber ensures that the fluid sample is introduced as a contiguous body, so as to enhance separation resolution. To ensure convenience and ease of switching, it is preferred that fluid communication is achieved through a sliding motion. Similarly, the integrated introducing means may comprise a valve constructed for actuation through a sliding motion. Rotational and linear sliding motion may be used in either case. In addition, mechanisms relating to on-device features that can be used to uptake sample from a sample source such as vials and titer plates may be employed as well in interfacing relation to the introduction means. See U.S. Ser. No. 09/570,948, inventors Zimmermann and Ple, filed on May 15, 2000.

Any of the above-described microdevices may separate the fluid sample according to one or more sample properties. For example, a component property may be molecular weight, polarity, hydrophobicity or charge. To enhance separation performance, the microdevice may include a mobile phase source, in fluid communication with the integrated introducing means and/or employed as a make-up fluid source. When the mobile phase source is employed in conjunction with the integrated introducing means, the integrated introducing means may provide fluid communication between the mobile phase source and the separation conduit through a bypass. This is particularly useful when a loading chamber is employed, insofar as loading of the chamber is made possible by providing the loading chamber in fluid communication with a sample source.

The microdevices may employ operation principles similar to those of ordinary liquid chromatography devices. Thus, there are instances in which ordinary liquid chromatography technology may be incorporated in the practice of the invention. For example, a fluid flow rate regulator for regulating flow rate may be employed to ensure that a mobile phase is delivered to the separation conduit at an appropriate rate and pressure. Such flow rate regulators may be interposed in the flow path between the mobile phase source and the integrated introducing means. The flow rate regulator may also include a flow splitter. Additionally, a flow sensor for determining and optionally controlling the rate of fluid flow into the sample inlet source may be provided. Similarly, as it is known in the art that more than one solvent may be employed to carry out ordinary liquid chromatography processes, the microdevice may include a mobile phase source comprises a mixer for mixing solvents. Further, temperature control means may provide reproducible separation performance.

In another embodiment of the invention, a method is provided for separating the components of a fluid sample. In order to carry out the method, a microdevice is provided as above. The method involves controllably introducing a predetermined volume of a fluid sample from a sample source into a sample inlet port, conveying the fluid sample through the conduit, thereby separating the components of the fluid sample; and analyzing the sample collected at the sample outlet port. An analyzer as described above is provided for carrying out the last step of the method.

From the above description of the various embodiments of the invention, it is evident that the integrated introducing means may introduce a predetermined volume of fluid sample appropriate to the desired separation process and the dimensions of the microdevice. Typically, the predetermined volume is less than about 5 microliters. Preferably, the predetermined volume is about 0.005 about 1 microliters. Optimally, the predetermined volume is about 0.01 to about 0.1 microliters. It should also be evident that the switching assembly provides for greater control in carrying out chemical or biochemical reactions and processes for sample preparation and analysis.

Thus, variations of the present invention will be apparent to those of ordinary skill in the art. For example, additional features may be included to carry out known reactions and processes, for example, reactions and processes associated with sample preparation, synthesis and analysis. Such features may be formed from conduits and channels that provide for fluid flow in a parallel or a nonparallel direction with respect to the contact surfaces. In addition, the integrated introducing means may be used to carry out digestion of the fluid sample before the sample is introduced into the separation conduit. That is, the conduit of the integrated introducing means may be filled with a moiety that digests the fluid sample. When the fluid sample contains peptidic moieties, commonly used proteolytic enzyme such as trypsin and pepsin may be employed. Similarly, when the fluid sample contains nucleotidic moieties, nuclease enzymes capable of nucleotidic digestion, e.g., endonucleases and exonucleases may be used. Moreover, additional substrates of a variety of shapes may be employed. Locking mechanisms may also be provided in order to provide a greater degree of control over the position of the contact surfaces of the switching assembly.

It is to be understood that while the invention has been described in conjunction with the preferred specific embodiments thereof, that the foregoing description is intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

We claim:

1. A microdevice assembly for separating the components of a fluid sample, the assembly comprising:
   a microdevice comprising:
      a substrate having first and second opposing surfaces and first and second microchannels formed in the first surface;
      a cover plate arranged over the first surface, the cover plate in combination with the first and second microchannels defining first and second conduits, respectively, the cover plate comprising a linear channel disposed therein;
      a sample inlet port in fluid communication with a valve, wherein the valve is constructed for selectively providing fluid communication from the inlet port to either one of the conduits to allow a fluid sample introduced from a sample source to be conveyed in a defined sample flow path such that the fluid sample travels, in order, through the sample inlet port, an integrated introducing means, the selected conduit and a sample outlet port associated with the selected conduit; and
      wherein the integrated introducing means is an integrated introducing means for mechanically, controllably introducing a predetermined volume of the fluid sample from the sample inlet port through a sample loading chamber of the integrated introducing means and through the selected conduit, and wherein the integrated introducing means comprises a switching plate comprising
         a first contact surface and an opposing contact surface, three curved fluid-transporting channels located on the first contact surface lying along a circle having a diameter equal in length to the linear channel in the cover plate;

wherein at least one of the conduits is constructed for separating the components of the fluid sample according to a component property, and an external device is interfaced with and in communication with the microdevice via an electrospray nozzle.

2. The microdevice of claim 1, wherein the electrospray nozzle is an ionizer.

3. The microdevice of claim 1, wherein each of the conduits is constructed for separating the components of the fluid sample according to a different component property.

4. A microdevice for separating the components of a fluid sample, the microdevice comprising:

a substrate having first and second opposing surfaces and first and second microchannels formed in the first surface;

a cover plate arranged over the first surface, the cover plate in combination with the first and second microchannels defining first and second conduits, respectively, the cover plate comprising a linear channel disposed therein;

a sample inlet port in fluid communication with the first conduit;

a first integrated introducing means for mechanically, controllably introducing the fluid sample from the sample inlet port, through the first integrated introducing means and through the first conduit, and wherein the first integrated introducing means comprises a switching plate comprising a first contact surface and an opposing contact surface, three curved fluid-transporting channels located on the first contact surface lying along a circle having a diameter equal in length to the linear channel in the cover plate; and a second integrated introducing means for controllably introducing the fluid sample from the first conduit through the second conduit to an outlet port, and wherein at least one of the conduits is constructed for separating the components of the fluid sample according to a component property.

5. The microdevice of claim 4, wherein the switching plate is arranged to result in a first flow path configuration or a second flow path configuration.

6. The microdevice of claim 5, wherein the first flow path configuration through the integrated introducing means provides a means to deliver mobile phase to the separation conduit.

7. The microdevice of claim 5, wherein the first flow path configuration through the integrated introducing means provides a means to deliver fluid sample to the separation conduit.

8. The microdevice of claim 5, wherein the sample loading chamber of the integrated introducing means comprises a conduit common to the first and second flow path configuration.

9. The microdevice of claim 5, wherein in the second flow path configuration, the sample loading chamber is disposed between an input port of the integrated introducing means and the separation conduit.

10. The microdevice of claim 9, wherein insertion of the sample loading chamber between an input port of the integrated introducing means and the separation conduit enables delivery of a precise amount of fluid sample to the separation conduit.

11. A microdevice for separating the components of a fluid sample, the microdevice comprising:

a substrate comprising first and second opposing surfaces and a microchannel formed in the first surface, the microchannel comprising a sample inlet terminus at a first end and a conduit at the sample inlet terminus, and five conduits extending through the substrate that, in combination with the sample inlet port represent the vertices of an equilateral hexagon;

a cover plate arranged over the first surface, the cover plate in combination with the microchannel defining a separation conduit constructed for separating the components of the fluid sample according to a component property, the cover plate comprising a sample inlet port in fluid communication with the separation conduit, a waste port in fluid communication with a conduit of the substrate, a mobile phase inlet in fluid communication with a conduit of the substrate, and a linear channel, wherein in each of the inlet port, waste port, and mobile phase inlet are located the same distance from a center point of the linear channel; and a switching plate comprising a first contact surface and an opposing contact surface, three curved fluid-transporting channels located on the first contact surface lying along a circle having a diameter equal to the length of the linear channel of the cover plate;

wherein the sample inlet port allows a fluid sample introduced from a sample source to be conveyed in a defined sample flow path such that the fluid sample travels, in order, through the sample inlet port, a switching plate configured to mechanically, controllably introduce a volume of the fluid sample, the separation conduit, and a sample outlet port.

12. The microdevice of claim 11, wherein the switching plate further comprises a handle that extends outwardly from a center of the three curved fluid-transporting channels.

13. The inicrodevice of claim 4, further comprising an interface that is structurally capable of being in communication with an external device.

14. The microdevice of claim 13, wherein the interface is an electrospray nozzle.

15. The microdevice of claim 11, further comprising a polymeric material formed in situ within the separation conduit.

16. The microdevice of claim 11, wherein the component property is selected from the group consisting of molecular weight, polarity, hydrophobicity and charge.

17. The microdevice of claim 11, wherein the integrated introducing means comprises a valve constructed for actuation through a sliding motion.

18. The microdevice of claim 17, wherein the valve is constructed for actuation through rotational motion.

19. A method for separating the components of a fluid sample, comprising:

(a) providing a microdevice comprising a substrate having first and second opposing surfaces and a microchannel formed in the first surface, a cover plate arranged over the first surface, the cover plate in combination with the microchannel defining a conduit constructed for separating the components of the fluid sample according to a component property, the cover plate comprising a linear channel disposed therein, and a sample inlet port in fluid communication with the conduit, wherein the sample inlet port allows a fluid sample introduced from a sample source to be conveyed in a defined sample flow path such that a fluid sample travels, in order, through the sample inlet port, a switching plate, the conduit, and a sample outlet port;

(b) mechanically, controllably introducing a predetermined volume of the fluid sample from the sample inlet port, through the switching plate, and through the conduit, wherein the switching plate comprises a first contact surface and an opposing contact surface, three curved fluid-transporting channels located on the first contact surface lying along a circle having a diameter equal in length to the linear channel in the cover plate;

(c) conveying the fluid sample through the conduit, thereby separating the components of the fluid sample;

(d) interfacing an external device with microdevice via an electrospray nozzle; and (e) analyzing the fluid sample flowing in the flow path or from the sample outlet port with the external device.

* * * * *